United States Patent [19]

Andersen et al.

[11] Patent Number: 6,043,239
[45] Date of Patent: *Mar. 28, 2000

[54] HETEROCYCLIC COMPOUNDS

[75] Inventors: Knud Erik Andersen, Smørum; Uffe Bang Olsen, Vallensbæk; Hans Petersen, Vanløse; Frederik Christian Grønvald, Vedbæk, all of Denmark; Ursula Sonnewald, Trondheim, Norway; Tine Krogh Jørgensen, Herlev; Henrik Sune Andersen, Københaven Ø, both of Denmark

[73] Assignee: Novo Nordisk A/S, Bagsvaerd, Denmark

[ * ] Notice: This patent is subject to a terminal disclaimer.

[21] Appl. No.: 09/012,918

[22] Filed: Jan. 23, 1998

Related U.S. Application Data

[60] Continuation of application No. 08/544,682, Oct. 8, 1995, Pat. No. 5,795,888, which is a division of application No. 08/367,648, Jan. 3, 1995, Pat. No. 5,595,989.

[30] Foreign Application Priority Data

Jan. 4, 1994 [DK] Denmark .................................. 0019/94
Nov. 9, 1994 [DK] Denmark .................................. 1290/94

[51] Int. Cl.[7] .......................... A61K 31/55; A61K 31/54; A61K 31/445; C07D 417/06; C07D 401/06
[52] U.S. Cl. ........................................... 514/225.5; 544/46
[58] Field of Search .............................. 544/46; 514/225.5

[56] References Cited

U.S. PATENT DOCUMENTS

| | | | |
|---|---|---|---|
| 2,877,224 | 3/1959 | Jacob | 544/46 |
| 2,921,069 | 1/1960 | Ullyot | 544/46 |
| 2,931,810 | 4/1960 | Yale | 544/46 |
| 2,957,870 | 10/1960 | Cusic et al. | 544/46 |
| 3,130,194 | 4/1964 | Jacob | 544/46 |
| 3,177,211 | 4/1965 | Zenitz et al. | 544/42 |
| 3,305,547 | 2/1967 | Stach et al. | 544/46 |
| 5,795,888 | 8/1998 | Anderson | 544/46 |

OTHER PUBLICATIONS

Andersen et al., J. Med. Chem., vol. 36, p. 1716–1725, 1993.
Nakanishi et al., J. Med. Chem., vol. 13, No. 4, pp. 644–648, 1979.

*Primary Examiner*—Mark L. Berch
*Attorney, Agent, or Firm*—Steve T. Zelson; Carol E. Rozek

[57] ABSTRACT

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

5 Claims, No Drawings

HETEROCYCLIC COMPOUNDS

CROSS-REFERENCE TO RELATED APPLICATIONS

This application is a continuation of U.S. application Ser. No. 08/544,682 filed Oct. 8, 1995 now U.S. Pat. No. 5,795,888 which is a division of U.S. application Ser. No. 08/367,648 filed Jan. 3, 1995, now U.S. Pat. No. 5,595,989, and claims priority under 35 U.S.C. 119 of Danish application nos. 0019/94 and 1290/94 filed Jan. 4, 1994 and Nov. 9, 1994, respectively, the contents of which are fully incorporated by reference.

The present invention relates to novel N-substituted azaheterocyclic carboxylic acids and esters thereof in which a substituted alkyl chain forms part of the N-substituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastrointestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastro-intestinal diseases or migraine.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

In addition to the above cited references, U.S. Pat. No. 3,074,953 discloses 1-(3-(10,11-dihydro-5H-dibenzo[a,d] cyclohepten-5-ylidene)-1-propyl)-4-phenyl-4-piperidinecarboxylic acid ethyl ester as a psychotropic drug. Analogous 1-substituted 4-phenyl-4-piperidinecarboxylic acid ester derivatives to the above cited compound are described (J. Med. Chem. 1967, 10, 627–635 and J. Org. Chem. 1962, 27, 230–240) as analgesics, antispasmodics and psychotropics. In JP 49032544, JP 48040357, FR 2121423, GB 1294550 and DE 2101066, 1-substituted 4-dialkylamino-4-piperidinecarboxamides are disclosed as psychotropic agents, for the treatment of schizophrenia and as inhibitors of inflammation.

DESCRIPTION OF THE INVENTION

The present invention relates to novel N-substituted azaheterocyclic carboxylic acids and esters thereof of formula I

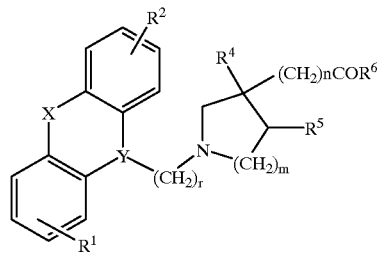

wherein $R^1$ and $R^2$ independently are hydrogen, halogen, trifluoromethyl, $C_{1-6}$-alkyl or $C_{1-6}$-alkoxy; Y is >N—$CH_2$—, >CH—$CH_2$— or >C=CH— wherein only the underscored atom participates in the ring system; X is —O—, —S—, —$CR^7R^8$—, —$CH_2CH_2$—, —CH=CH—$CH_2$—, —$CH_2$—CH=CH—, —$CH_2CH_2CH_2$—, —CH=CH—, —$NR^9$—(C=O)—, —O—$CH_2$—, —(C=O)— or —(S=O)— wherein $R^7$, $R^8$ and $R^9$ independently are hydrogen or $C_{1-6}$-alkyl; r is 1, 2, or 3; m is 1 or 2 and n is 1 when m is 1 and n is 0 when m is 2; $R^4$ and $R^5$ each represents hydrogen or may—when m is 2—together represent a bond; and $R^6$ is OH or $C_{1-8}$-alkoxy; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

As used herein, the term "patient" includes any mammal which could benefit from treatment of neurogenic inflammation. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.: Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

The compounds of formula I may be prepared by the following method:

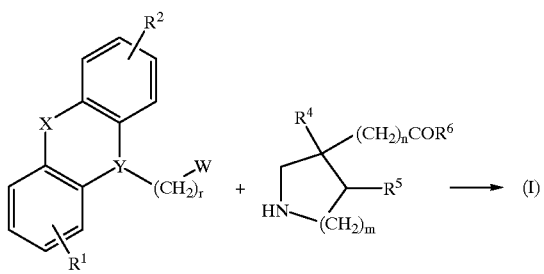

A compound of formula II wherein $R^1$, $R^2$, X, Y, and r are as defined above and W is a suitable leaving group such as halogen, p-toluene sulphonate or mesylate may be reacted with an azaheterocyclic compound of formula III wherein $R^4$, $R^5$, $R^6$, m and n are as defined above. This alkylation reaction may be carried out in a solvent such as acetone, dibutylether, 2-butanone, methyl ethyl ketone, ethyl acetate, tetrahydrofuran (THF) or toluene in the presence of a base e.g. potassium carbonate and a catalyst, e.g. an alkali metal iodide at a temperature up to reflux temperature for the solvent used for e.g. 1 to 120 h. If esters have been prepared in which $R^6$ is alkoxy, compounds of formula I wherein $R^6$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances It may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

Pharmacological Methods

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 µl 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Values for inhibition of formalin induced pain response for some representative compounds are recorded in table 1.

TABLE 1

Inhibition of formalin induced pain response at 0.1 mg/kg

| Example no. | % Pain inhibition |
|---|---|
| 4 | 50 |
| 5 | 13 |
| 7 | 35 |
| 10 | 35 |
| 11 | 29 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent.

The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patents, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9-40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography and THF is tetrahydrofuran, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. $^1$H-NMR shifts ($\delta_H$) are given in parts per million (ppm). M.p. is melting point and is given in °C. and is not corrected. Column chromatography was carried out using the technique described by W. C. Still et al, J. Org. Chem. (1978), 43, 2923–2925 on Merck silica gel 60 (Art. 9385). HPLC analysis was performed using a 5 μm C18 4×250 mm column, eluting with a 20–80% gradient of 0.1% trifluoroacetic acid/acetonitrile and 0.1% trifluoroacetic acid/water over 30 minutes at 35° C. Compounds used as starting materials are either known compounds or compounds which can readily be prepared by methods known per se.

Example 1a (R)-1-(3-(10,11-Dihydro-5H-dibenzo[a,d] cyclohepten-5-ylidene)-1-propyl)-3-piperidinecarboxylic Acid Hydrochloride A solution of cyclopropylmagnesium bromide in dry THF (prepared from cyclopropylbromide (12.1 g, 0.10 mol), magnesium turnings (2.45 g, 0.10 mol) and dry THF (65 ml)) was placed under an atmosphere of nitrogen. A solution of 10,11-dihydro-5H-dibenzo[a,d]cyclohepten-5-one (10.4 g, 0.05 mol) in dry THF (25 ml) was added dropwise and when addition was complete the mixture was heated at reflux for 30 minutes. The reaction mixture was cooled on an ice-bath and saturated ammonium chloride (50 ml) was carefully added. The mixture was neutralized with 2N hydrochloric acid and extracted with diethyl ether (2×200 ml). The combined organic extracts were dried ($Na_2SO_4$) and the solvent was evaporated in vacuo to give 13.1 g of crude 5-cyclopropyl-10,11-dihydro-5H-dibenzo[a,d]cyclohepten-5-ol.

The above crude alcohol (13.1 g) was dissolved in dichloromethane (150 ml) and a solution of trimethylsilyl bromide (9.2 g, 0.06 mol) in dichloromethane (50 ml) was added dropwise. When addition was complete the mixture was stirred at room temperature for 15 minutes and water (50 ml) was added. The phases were separated and the organic phase was washed with saturated sodium bicarbonate (2×50 ml). The organic phase was dried ($Na_2SO_4$) and the solvent was evaporated in vacuo to give 16.5 g of crude 5-(3-bromo-1-propylidene)-10,11-dihydro-5H-dibenzo[a,d]cycloheptene as a solid.

A mixture of the above crude bromide (6.3 g, 20 mmol), ethyl (R)-3-piperidinecarboxylate (4.7 g, 30 mmol), potassium carbonate (5.5 g, 40 mmol) and acetone (50 ml) was stirred at room temperature for 124 h. The mixture was filtered and the solvent was evaporated in vacuo. The oily residue was purified on silica gel (200 g, ethyl acetate/n-heptane=1/1) to give 4.4 g of (R)-1-(3-(10,11-dihydro-5H-dibenzo[a,d]cyclohepten-5-ylidene)-1-propyl)-3-piperidinecarboxylic acid ethyl ester as an oil. $R_f$=0.38 ($SiO_2$;-ethyl acetate/n-heptane 1:1).

The above ester (4.4 g, 11 mmol) was dissolved in ethanol (40 ml) and 4N sodium hydroxide (8.3 ml) was added. The mixture was stirred vigorously at ambient temperature for 7 h. Dichloromethane (700 ml) was added followed by 2.5N hydrochloric acid until pH 1. The phases were separated, the organic phase dried ($MgSO_4$) and the solvent was evaporated in vacuo. The residue was re-evaporated twice with acetone and then triturated with a mixture of acetone and diethyl ether. The solid was isolated by filtration and dried in air to give 2.2 g of the title compound as a solid.

M.p. 206–208° C. Calculated for $C_{24}H_{27}NO_2$, HCl: C, 72.4%; H, 7.1%; N, 3.5%; Found: C, 72.1%; H, 7.3%; N, 3.3%.

By a similar procedure as described in Example 1a the following compounds have been prepared:

Example 1b (S)-1-(3-(10,11-Dihydro-5H-dibenzo[a,d] cyclohepten-5-ylidene)-1-propyl)-3-piperidinecarboxylic Acid Dihydrochloride M.p. 216–218° C. $^1$H-NMR (200 MHz, DMSO-$d_6$) $\delta_H$ 1.43 (bs, 1H), 1.78 (bs, 2H), 1.96 (bs, 1H), 2.5 (bd, 1H, CH—COOH), 2.84 (bm, 2H), 3.16 (bs, 2H), 3.26 (bs, 4H), 3.34 (s, 4H), 5.78 (t, 1H), 7.07 (dd, 1H, C=CH—$CH_2$), 7.12–7.29 (m, 7H).

Example 1c 1-(3-(10,11-Dihydro-5H-dibenzo[a,d]cyclohepten-5-ylidene)-1-propyl)-1,2,5,6-tetrahydro-3-pyridinecarboxylic Acid Hydrochloride M.p. 140–145° C. Calculated for $C_{24}H_{25}NO_2$, HCl, $C_3H_6O$: C, 71.4%; H, 7.1%; N, 3.1%; Found: C, 71.5%; H, 6.9%; N, 3.1%.

Example 1d (R)-1-(3-(Fluoren-9-ylidene)-1-propyl)-3-piperidinecarboxylic Acid Hydrochloride M.p. 217–219° C. Calculated for $C_{22}H_{23}NO_2$, HCl, 1/4$H_2O$: C, 70.6%; H, 6.5%; N, 3.7%; Cl, 9.5%; Found: C, 70.8%; H, 6.6%; N, 3.5%; Cl, 9.4%.

Example 1e (R)-1-(3-(3-Methyl-10,11-dihydro-5H-dibenzo[a,d] cyclohepten-5-ylidene)-1-propyl)-3-piperidinecarboxylic Acid Hydrochloride M.p. 218–221° C. Calculated for $C_{24}H_{29}NO_2$, HCl: C, 72.87%; H, 7.35%; N. 3.40%; Found: C, 72.60%; H, 7.58%; N, 3.24%.

Example 2

1-(3-(5H-Dibenzo[a,d]cyclohepten-5-ylidene)-1-propyl)-3-piperidinecarboxylic Acid Sodium Salt A solution of cyclopropylmagnesium bromide in dry THF (prepared from cyclopropylbromide (8.0 g, 0.067 mol), magnesium turnings (1.3 g, 0.053 mol) and dry THF (35 ml)) was placed under an atmosphere of nitrogen. A solution of 5H-dibenzo[a,d]cyclohepten-5-one (6.0 g, 0.028 mol) in dry THF (15 ml) was added dropwise and when addition was complete the mixture was heated at reflux for 30 minutes. The reaction mixture was cooled on an ice-bath and saturated ammonium chloride (35 ml) was carefully added. The mixture was diluted with water (50 ml) and extracted with diethyl ether (2×50 ml). The combined organic extracts were washed with water, dried ($Na_2SO_4$) and the solvent was evaporated in vacuo to give 8.6 g of crude 5-cyclopropyl-5H-dibenzo[a,d]cyclohepten-5-ol.

To the above crude alcohol (8.6 g) was added glacial acetic acid (60 ml). The mixture was cooled on an ice-bath and a mixture of glacial acetic acid (30 ml) and 47% hydrobromic acid (15 ml) was added-The mixture was stirred for 30 minutes, poured into water (300 ml) and extracted with diethyl ether (2×100 ml). The combined organic phases were washed with water, dried ($Na_2SO_4$) and the solvent was evaporated in vacuo to give a residue which was recrystallized from diethyl ether. This afforded 6.8 g of 5-(3-bromo-1-propylidene)-5H-dibenzo[a,d]cycloheptene as a solid. M.p. 88–89° C.

A mixture of the above bromide (5.0 g, 16 mmol), ethyl 3-piperidinecarboxylate (3.2 g, 20 mmol), potassium carbonate (7.3 g, 53 mmol) and acetone (150 ml) was heated at reflux for 15 h. The mixture was filtered and the solvent was evaporated in vacuo. The oily residue was dissolved in ethyl acetate (60 ml) and washed with 2N hydrochloric acid (2×30 ml). The organic phase was dried and the solvent evaporated in vacuo. The residue was dissolved in acetone (25 ml), treated with hydrogenchloride gas and the mixture was diluted with diethyl ether (120 ml). The solvent was decanted and the oily residue was dried in vacuo to give 5–6 g of 1-(3-(5H-dibenzo[a,d]cyclohepten-5-ylidene)-1-propyl)-3-piperidinecarboxylic acid ethyl ester hydrochloride as an amorphous solid.

The above ester (4.5 g, 11 mmol) was dissolved in ethanol (80 ml), 32% sodium hydroxide (180 ml) was added and the mixture was heated at reflux for 1 h. To the cooled reaction mixture a mixture of dichloromethane and ethyl acetate was added. The phases were separated and the aqueous phase was treated with activated charcoal and filtered through millipore (0.22 µm). The solvent was evaporated from the filtrate in vacuo and the residue was dissolved in a mixture of water and dichloromethane (1:3). The phases were separated, the organic phase dried ($MgSO_4$) and the solvent evaporated in vacuo. The residue was dissolved in water and freeze-dried to give 3.0 g of the title compound as an amorphous solid.

$^1$H-NMR (DMSO-$d_6$) δ 5.47 (t, 1H); 6.94 (s, 2H).

Example 3

1-(3-(Thioxanthen-9-ylidene)-1-propyl)-3-piperidinecarboxylic Acid Hydrochloride A solution of cyclopropylmagnesium bromide in dry THF (prepared from cyclopropylbromide (18.2 g, 0.15 mol), magnesium turnings (2.9 g, 0.12 mol) and dry THF (80 ml)) was placed under an atmosphere of nitrogen. A solution of thioxanthen-9-one (12.7 g, 0.06 mol) in dry THF (70 ml) was added dropwise and when addition was complete the mixture was heated at reflux for 20 minutes. The reaction mixture was cooled on an ice-bath and saturated ammonium chloride (70 ml) was carefully added. The mixture was diluted with water (100 ml) and extracted with diethyl ether (2×100 ml). The combined organic extracts were washed with water, dried ($Na_2SO_4$) and the solvent was evaporated in vacuo to give 25.2 g of crude 9-cyclopropyl-9H-thioxanthen-9-ol.

To the above crude alcohol (25.2 g) was added glacial acetic acid (120 ml). The mixture was cooled on an ice-bath and a mixture of glacial acetic acid (60 ml) and 47% hydrobromic acid (30 ml) was added. The mixture was stirred for 30 minutes, poured into water (600 ml) and extracted with diethyl ether (3×200 ml). The combined organic phases were washed with water, dried ($Na_2SO_4$) and the solvent was evaporated in vacuo to give 19.5 g of crude 9-(3-bromo-1-propylidene)-9H-thioxanthene. $R_f$=0.35 ($SiO_2$; THF/heptane=1:9).

A mixture of the above crude bromide (2.0 g, 6.3 mmol), ethyl 3-piperidinecarboxylate (1.2 g, 7.5 mmol), potassium carbonate (2.9 g, 21 mmol) and acetone (60 ml) was stirred at ambient temperature for 3 h and then heated at reflux for 16 h. The mixture was filtered and the solvent was evaporated in vacuo. The oily residue was purified on silica gel (dichloromethane/methanol=98:2) to give 1.3 g of 1-(3-(thioxanthen-9-ylidene)-1-propyl)-3-piperidinecarboxylic acid ethyl ester as an oil. $R_f$=0.21 ($SiO_2$; dichloromethane/methanol=98:2).

The above ester (0.74 g, 1.8 mmol) was dissolved in ethanol (25 ml) and 40% sodium hydroxide (6 ml) was added. The mixture was heated at reflux for 1 h. 10% Hydrochloric acid (25 ml) was added followed by dichloromethane (150 ml). The phases were separated and the organic phase was washed with water, dried ($NaSO_4$) and the solvent was evaporated in vacuo to give 0.6 g of the title compound as a solid. M.p. 150–160° C. A sample was dissolved in acetone and precipitated with diethyl ether. The solid formed was isolated by filtration and dried in vacuo.

Calculated for $C_{22}H_{23}NO_2S$, HCl, $1/2H_2O$: C, 64.3%; H, 6.1%; N, 3.4%; Found: C, 64.0%; H, 6.2%; N, 3.5%. $^1$H-NMR (CDCl$_3$) δ 5.74 (t, 1H).

Example 4

(R)-1-(3-(10,11-Dihydro-5H-dibenz[b,f]azepin-5-yl)-1-propyl)-3-piperidinecarboxylic Acid Hydrochloride To a solution of 10,11-dihydro-5H-dibenz[b,f]azepine (8.1 g, 0.040 mol) in dry dibutyl ether (60 ml) kept under an atmosphere of nitrogen, sodium hydride (1.6 g, 0.040 mol, 60% oil dispersion) was carefully added. The reaction mixture was heated at reflux temperature for 4 h and then allowed to cool to 80° C. 3-Bromo-1-propyl tetrahydro-2-pyranyl ether (10.7 g, 0.048 mol) was added and the mixture was heated at reflux temperature for 16 h. To the cooled reaction mixture was added water (20 ml) and the phases were separated. From the organic phase the solvent was evaporated and the residue was dissolved in a mixture of methanol (150 ml) and a 4N HCl solution (50 ml). The mixture was heated at reflux temperature for 15 minutes and then stirred for 1 h at ambient temperature. Water (250 ml) was added and the mixture was extracted with ethyl acetate (2×200 ml). The combined organic extracts were dried ($Na_2SO_4$), filtered and the solvent evaporated in vacuo. This afforded a residue which was purified further by chromatography on silica gel (200 g) using a mixture of n-heptane and ethyl acetate (3:2) as eluent to give 5.5 g of 3-(10,11-dihydro-5H-dibenz[b,f]azepin-5-yl)-1-propanol as an oil. $R_f$: 0.30 (SiO$_2$; n-heptane/ethyl acetate=1:1).

The above alcohol (3.0 g, 12 mmol) was dissolved in toluene (100 ml) and triethylamine (4.0 ml) was added. Methanesulfonyl chloride (1.5 g, 19 mmol) was added dropwise and when addition was complete the reaction mixture was stirred for 2 h. Water was added and the phases were separated. The organic phase was dried (MgSO$_4$) and the solvent was evaporated in vacuo to give a residue which was dissolved in acetone (50 ml). To this solution (R)-3-piperidinecarboxylic acid ethyl ester tartrate (5.4 g, 18 mmol) and potassium carbonate (4.1 g, 30 mmol) were added and the mixture was heated at reflux for three days. The mixture was allowed to cool, then filtered and the solvent evaporated in vacuo to give a residue which was dissolved in diethyl ether. The resulting mixture was extracted with a 5% tartaric acid solution (2×100 ml). The combined aqueous extracts were washed with diethyl ether and pH was adjusted to 7–8 with potassium carbonate solution. The neutralised aqueous mixture was extracted with ethyl acetate (2×200 ml). The combined ethyl acetate extracts were washed with water, brine and dried (MgSO$_4$). The solvent was evaporated in vacuo to give a residue which was dissolved in diethyl ether (50 ml) and filtered through silica gel. This afforded 2.8 g of (R)-1-(3-(10,11-dihydro-5H-dibenz[b,f]azepin-5-yl)-1-propyl)-3-piperidinecarboxylic acid ethyl ester as an oil.

The above ester (2.8 g, 7.1 mmol) was dissolved in ethanol (10 ml) and 4N sodium hydroxide (5.3 ml) was added. The mixture was stirred at ambient temperature for 10 h and concentrated hydrochloric acid was added until acidic reaction (pH 1). The resulting mixture was extracted with dichloromethane (300 ml) and the organic extract was dried (MgSO$_4$). The solvent was evaporated in vacuo to give a foamy residue which was re-evaporated with acetone. This afforded 2.3 g of the title compound as an amorphous solid.

Calculated for C$_{23}$H$_{28}$N$_2$O$_2$, HCl, H$_2$O: C, 65.9%; H, 7.5%; N, 6.7%; Found: C, 66.1%; H, 7.6%; N, 6.2%.

Example 5

(R)-1-(4-(10,11-Dihydro-5H-dibenzo[b,f]azepin-5-yl)-1-butyl)-3-piperidinecarboxylic Acid Hydrochloride To a solution of 10,11-dihydro-5H-dibenzo[b,f]azepine (16.2 g, 0.083 mol) in dry dibutyl ether (120 ml) kept under an atmosphere of hydrogen, sodium hydride (3.2 g, 0.08 mol, 60% dispersion in oil) was carefully added. The reaction mixture was heated at reflux temperature for 4 h and then allowed to cool to 80° C. 4Chloro-1-butyl tetrahydro-2-pyranyl ether (18.5 g, 0.096 mol) was added and the mixture heated at reflux temperature for 16 h. After cooling to room temperature, water (40 ml) was added, and the phases were separated. The organic phase was evaporated until dryness. The residue was dissolved in a mixture of methanol (300 ml) and 4N HCl (100 ml). The mixture was heated at reflux temperature for 15 minutes and then stirred for 1 h at room temperature. Water (500 ml) was added and the mixture was extracted with ethyl acetate (6×200 ml). The combined organic extracts were dried (Na$_2$SO$_4$), filtered and the solvent evaporated. This afforded a residue which was purified by column chromatography on silica gel (400 g) using a mixture of n-heptane and ethyl acetate (3:2) as eluent. 13.1 g (59%) of 4-(10,11-dihydro-5H-dibenzo[b,f]azepin-5-yl)-1-butanol was obtained as an oil, that solidified upon cooling in a refrigerator overnight. $R_f$: 0.34 (SiO$_2$; n-heptane/ethyl acetate=1:1).

The above alcohol (5.4 g, 0.02 mol) was dissolved in toluene (160 ml) and triethylamine (7 ml) was added. Methanesulfonyl chloride (2.5 ml, 0.032 mol) was added dropwise and when addition was complete the reaction mixture was stirred for 2 h. Water was added and the phases were separated. The organic phase was dried (MgSO$_4$) and the solvent evaporated in vacuo affording a residue which was dissolved in acetone (85 ml). To this solution (R)-3-piperidinecarboxylic acid ethyl ester tartrate (9.0 g, 0.03 mol) and potassium carbonate (7.0 g, 0.051 mol) were added and the mixture was heated at reflux temperature for 16 h. After cooling to room temperature and filtration on filter aid (celite) the solvent was removed by evaporation. The residue was dissolved in diethyl ether (100 ml) and extracted with a 5% tartaric acid solution (3×125 ml). The combined aqueous extracts were washed with diethyl ether and pH was adjusted to 7–8 with a potassium carbonate solution. The neutralised aqueous mixture was extracted with ethyl acetate (4×200 ml). The combined ethyl acetate extracts were washed with water, brine and dried (MgSO$_4$). The solvent was evaporated in vacuo affording 2.6 g (32%) of 1-(4(10,11-dihydro-5H-dibenzo[b,f]azepin-5-yl)-1-butyl]-3-piperidinecarboxylic acid ethyl ester, obtained as an oil. The residue was purified further by column chromatography on silica gel (65 g) using a mixture of dichloromethane and methanol (99.2:0.8) as eluent. $R_f$: 0.20 (SiO$_2$; n-heptane/ethyl acetate=1:1).

The above ester (1.5 g, 0.0037 mol) was dissolved in ethanol (10 ml) and a solution of NaOH (0.52 g) in water (2 ml) was added. The mixture was stirred at room temperature for 2 h. Concentrated HCl was added until pH<1 (2 ml). Dichloromethane (75 ml) was added, followed by water (50 ml) and the phases were separated. The organic phase was dried (MgSO$_4$) and the solvent evaporated in vacuo. Acetone (15 ml) was added to the residue which was re-evaporated. Acetone (30 ml) was added to the dry white product, affording, after filtration and drying, 1.3 g (84%) of the title compound as a white solid.

M.p. 222–224° C. Calculated for C$_{24}$H$_{30}$N$_2$O$_2$, HCl: C, 69.47%; H, 7.53%; N, 6.75%; Found: C, 69.26%; H, 7.88%; N, 6.50%.

Example 6

(R)-1-(2-(10,11-Dihydro-5H-dibenzo[b,f]azepin-5-yl)ethyl)-3-piperidinecarboxylic Acid Hydrochloride In a 500 ml roundbottom flask equipped with magnetical stirring, thermometer, addition funnel and scrubber 10,11-dihydro-5H-dibenzo[b,f]azepine (19.5 g, 0.10 mol) was dissolved in dry toluene (100 ml). Chloroacetyl chloride (13.6 g 0.12 mol) was slowly added. The reaction mixture was heated to 9$_5$° C. for 30 minutes and then allowed to cool to room temperature. Under stirring, 0.2N NaOH (50 ml) was added. More toluene was added (100 ml) and the phases were separated. The organic phase was washed with 0.2N NaOH (3×50 ml) until pH>10, and then with water (3×50 ml) and brine (50 ml). After drying (MgSO$_4$) the organic phase was evaporated in vacuo affording an oily residue that crystallised upon standing overnight The product was obtained in quantitative yield and used for further reactions without purification.

The above crude amide (20.0 g, 0.074 mol) was dissolved in dry THF (150 ml) under a nitrogen atmosphere and cooled to 5° C. Sodium borohydride (2.3 g, 0.06 mol) was added followed by slow dropwise addition of $BF_3.Et_2O$ (9.4 ml, 0.076 mol). The reaction mixture was left stirring overnight. Further amounts of $NaBH_4$ (2.0 g. 0.053 mol) and $BF_3.Et_2O$ (6 ml, 0.049 mol) were added, and stirring was continued overnight. Methanol (20 ml) was added dropwise and stirring was continued for 1 h. Water (80 ml) was added to dissolve precipitated salt, followed by ethyl acetate (100 ml). The phases were separated, and the aqueous phase was extracted with ethyl acetate (2×100 ml). The combined organic extracts were washed with water (4×100 ml) and brine (100 ml). The solvent was evaporated in vacuo and the residue was stripped twice with toluene. The crude product was purified by column chromatography on silica gel (400 g) using dichloromethane as eluent. This afforded 15.0 g (79%) of 5-(2-chloroethyl)-10,11-dihydro-5H-dibenzo[b,f] azepine. $R_f$: 0.70 ($SiO_2$; dichloromethane).

The above chloride (10.0 g, 0.039 mol) was dissolved in acetone (175 ml) and potassium iodide (3.3 g) was added. To this solution (R)-3-piperidinecarboxylic acid ethyl ester tartrate (18.0 g, 0.06 mol) and potassium carbonate (14.0 g, 0.12 mol). were added and the mixture was heated at reflux temperature for 72 h. After cooling to room temperature and filtration on filter aid (celite) the solvent was removed by evaporation. The residue was purified by column chromatography on silica gel (300 g) using a mixture of heptane and ethyl acetate (1:1) as eluent. This afforded 1.6 g (11%) of (R)-1-(2-(10,11-dihydro-5H-dibenzo[b,f]azepin-5-yl) ethyl)-3-piperidinecarboxylic acid ethyl ester as an oil. $R_f$: 0.34 ($SiO_2$; n-heptane/ethyl acetate=1:1).

The above ester (1.28 g, 0.0034 mol) was dissolved in ethanol (10 ml) and a solution of NaOH (0.52 g) in water (2 ml) was added. The mixture was stirred at room temperature for 2 h. Concentrated HCl was added until pH<1 (2 ml). Dichloromethane (75 ml) was added, followed by water (50 ml) and the phases were separated. The organic phase was dried ($MgSO_4$) and the solvent evaporated in vacuo. Acetone (15 ml) was added to the residue which was re-evaporated. Acetone (30 ml) was added to the dry white product, affording, after filtration and drying, 1.1 g (80%) of the title compound as a white solid.

M.p. 246–248° C. Calculated for $C_{22}H_{26}N_2O_2$, HCl, 1/4 $H_2O$: C, 67.44%; H, 7.02%; N. 7.15%; Found: C, 67.72%; H, 7.23%; N, 7.01%.

Example 7

(R)-1-(3-(3-Chloro-10,11-dihydro-5H-dibenzo[b,f] azepin-5-yl)-1-propyl)-3-piperidinecarboxylic Acid Hydrochloride In a 100 ml roundbottom flask equipped with magnetical stirring, thermometer, nitrogen-inlet and addition funnel, 3-chloro-10,11-dihydro-5H-dibenzo[b,f]azepine (1.3 g, 0.0056 mol) was dissolved in dry toluene (30 ml). Under nitrogen, ethyl malonyl chloride (1.01 g, 0.0067 mol) was slowly added. The reaction mixture was heated at reflux temperature for 2 h and then allowed to cool to room temperature. Under stirring, 0.2N NaOH (2.5 ml) and water (30 ml) was added. More toluene was added (100 ml) and the phases were separated. The organic phase was washed with water (3×50 ml) and brine (50 ml). After drying ($MgSO_4$) the organic phase was evaporated in vacuo affording an oily residue. The product was obtained in quantitative yield and used for further reactions without purification.

$LiAlH_4$ (920 mg, 0.024 mol) was placed in a dry 250 ml three-necked roundbottom flask, equipped with thermometer, magnetical stirring and addition funnel. Under nitrogen dry toluene (40 ml) was added followed by slow addition of THF (4 ml). A temperature at 15–25° C. was assured by the use of a water/ice-bath. The above amide (2.1 g, 0.0061 mol) was dissolved in dry THF (12 ml) and slowly added to the $LiAlH_4$-slurry. The temperature was kept at 20–25° C. The reaction mixture was left stirring overnight at room temperature. Water (1 ml) was added dropwise, followed by 4N NaOH (1 ml) and finally water (3 ml). The resulting precipitate was filtered off on filter aid (celite) and the toluene solution was dried ($MgSO_4$). The crude product was purified by column chromatography on silica gel (75 g) using a mixture of heptane and ethyl acetate (1:1) as eluent. This afforded 0.9 g (50%) of 3-(3-chloro-10,11-dihydro-5H-dibenzo[b,f]azepin-5-yl)-1-propanol as an oil. $R_f$: 0.36 ($SiO_2$; n-heptane/ethyl acetate=1:1).

The above alcohol (870 mg, 0.003 mol) was dissolved in toluene (25 ml) and triethylamine (1 ml) was added. Methanesulfonyl chloride (0.5 ml, 0.006 mol) was added dropwise and the reaction mixture was stirred for 2 h. Water (100 ml) was added, followed by further amounts of toluene (100 ml) and the phases were separated. The organic phase was dried ($MgSO_4$) and the solvent evaporated in vacuo affording a residue which was dissolved in methyl ethyl ketone (50 ml). To this solution (R)-3-piperidinecarboxylic acid ethyl ester tartrate (1.4 g, 0.0047 mol) and potassium carbonate (1.0 g, 0.0072 mol) were added and the mixture was heated at reflux for 24 h, and left stirring at room temperature for 24 h. After filtration on filter aid (celite) the solvent was removed by evaporation. The residue was purified by column chromatography on silica gel (100 g) using a mixture of heptane and ethyl acetate (1:1) as eluent. This afforded 1.0 g (79%) of (R)-1-(3-(3-chloro-10,11-dihydro-5H-dibenzo[b, f]azepin-5-yl)-1-propyl)-3-piperidinecarboxylic acid ethyl ester as an oil. $R_f$: 0.34 ($SiO_2$; n-heptane/ethyl acetate=1:1)

The above ester (500 mg, 0.0012 mol) was dissolved in ethanol (4 ml) and a solution of NaOH (0.2 g) in water (1 ml) was added. The mixture was stirred at room temperature for 2 h. Concentrated HCl was added until pH<1 (0.75 ml). Dichloromethane (75 ml) was-added followed by water (50 ml) and the phases were separated. The organic phase was dried ($MgSO_4$) and the solvent evaporated in vacuo. The residue crystallized upon addition of ethyl acetate, affording, after filtration and drying, 0.4 g (68%) of the title compound as a white solid.

M.p. 135–138° C. Calculated for $C_{23}H_{27}N_2O_2$, HCl, 3/4 $H_2O$: C, 61.48%; H, 6.57%; N, 6.23%; Found: C, 61.35%; H, 6.67%; N, 5.70%.

Example 8a (R)-1-(3-(10H-Phenothiazin-10-yl)-1-propyl)-3-piperidinecarboxylic Acid Hydrochloride To a solution of phenothiazine (4.0 g, 0.02 mol) in dry dimethylformamide (100 ml) kept under an atmosphere of nitrogen, sodium hydride (1.0 g, 0.025 mol, 60% dispersion in oil) was carefully added. The reaction mixture was left stirring for 15 minutes. 1-Bromo-3-chloropropane (8.0 g, 0.05 mol) was added and the mixture was left stirring overnight. Ammonium chloride (2.0 g, 0.04 mol) was added, and after continued stirring for 30 minutes the solution was poured onto water (300 ml). The mixture was extracted with dichloromethane (2×200 ml). The combined organic extracts were dried ($MgSO_4$), filtered and the solvent evaporated. This afforded a residue which was purified by column chromatography on silica gel (250 g) using a mixture of n-heptane and ethyl acetate (9:1) as eluent. 4.4 g (80%) of 10-(3-chloropropyl)-10H-phenothiazine was obtained as an oil. $R_f$: 0.55 ($SiO_2$; n-heptane/ethyl acetate=1:1).

Potassium iodide (10.0 g, 0.06 mol) was dissolved in methyl ethyl ketone (100 ml) and heated at reflux temperature for 1 h. The above chloride (2.64 g, 0.09 mol) was dissolved in methyl ethyl ketone (10 ml) and added. The mixture was heated at reflux temperature for 3 h. After cooling to about 60° C., (R)-3-piperidinecarboxylic acid ethyl ester tartrate (2.64 g, 0.009 mol) and potassium carbonate (2.0 g, 0.014 mol) were added. The mixture was heated at reflux temperature for 24 h and left stirring at room temperature for 24 h. After filtration on filter aid (celite) the solvent was removed by evaporation. The residue was purified by column chromatography on silica gel (150 g) using a mixture of heptane and ethyl acetate (6:4) as eluent. This afforded 2.5 g (87%) of (R)-1-(3-(10H-phenothiazin-10-yl)-1-propyl)-3-piperidinecarboxylic acid ethyl ester as an oil. $R_f$: 0.20 ($SiO_2$; n-heptane/ethyl acetate=1:1).

The above ester (1.7 g, 0.0043 mol) was dissolved in ethanol (15 ml) and a solution of NaOH (0.63 g) in water (2.5 ml) was added. The mixture was stirred at room temperature for 2 h. Concentrated HCl was added until pH<1 (2.5 ml). Dichloromethane (100 ml) was added, followed by water (50 ml) and the phases were separated. The organic phase was dried ($MgSO_4$) and the solvent evaporated in vacuo. The residue crystallized upon addition of diethyl ether, followed by a small amount of dichloromethane. This afforded, after filtration and drying, 0.3 g (18%) of the title compound as a white solid. Subsequent re-evaporation of the filtrate afforded 1.08 g (62%) of the product.

M.p. 123°–128° C. Calculated for $C_{21}H_{25}N_2O_2S$, HCl, 5/4 $H_2O$: C, 58.95%; H, 6.43%; N, 6.55%; Found: C, 59.19%; H, 6.52%; N, 6.17%.

By a similar procedure as described in Example 8a the following compounds have been prepared:

Example 8b (R)-1-(3-(2-Trifluoromethyl-10H-phenothiazin-10-yl)-1-propyl)-3-piperidinecarboxylic Acid Hydrochloride M.p. 198–200° C. $^1$H-NMR (200 MHz, DMSO-$d_6$) $\delta_H$ 1.45 (bs, 1H), 1.79–2.13 (bm, 4H), 276–3.44 (bm, 8H), 4.06 (t, 2H), 7.02 (t, 1H), 7.12–7.42 (m, 6H).

Example 8c (R)-1-(3-(5-Oxo-10H-phenothiazin-10-yl)-1-propyl)-3-piperidinecarboxylic Acid Hydrochloride 10-(3-Chloropropyl)-10H-phenothiazine (2 g, 0.007 mol) was dissolved in glacial acetic acid (40 ml), 30% aqueous hydrogen peroxide (2.25 ml, 0.022 mol) was added and the mixture stirred for 48 h under an atmosphere of nitrogen. The reaction mixture was left overnight. Precipitated crystals were filtered off and washed with water (2×20 ml), diethyl ether (2×50 ml) and dried in vacuo. Yield 1.38 g (64%) of 10-(3-chloroproryl)-10H-phenothiazine 5-oxide as light brown crystals. M.p. 171–173° C.

$^1$H-NMR (200 MHz, $CDCl_3$) $\delta_H$ 2.35 (m, 2H), 3.63 (t, 2H), 4.43 (t, 2H), 7.25 (t, 2H), 7.40 (d, 2H), 7.61 (dt, 2H), 8.09 (dd, 2H).

The title compound was prepared using 10-(3-chloropropyl)-10H-phenothiazine 5-oxide instead of 10(3-chloropropyl)-10H-phenothiazine by a method similar to that described in Example 8a.

M.p. >280° C. $^1$H-NMR(400 MHz, DMSO-$d_6$) $\delta_H$ 1.46 (bd, 1H), 1.84 (bs, 2H), 2.01 (bd, 1H), 2.28 (bs, 2H), 2.89 (bd, 2H), 3.39 (bm, 2H), 3.54 (bd, 1H), 4.39 (t, 2H, N—$CH_2$—$CH_2$—), 7.41 (m, 2H), 7.79 (d, 4H), 8.03 (d, 2H), 10.95 (bs, 1H), 12.85 (bs, 1H).

Example 9

(R)-1-(3-(10H-Phenoxazin-10-yl)-1-propyl)-3-piperidinecarboxylic Acid Hydrochloride To a solution of phenoxazine (3.7 g, 0.02 mol) in dry dimethylformamide (100 ml) kept under an atmosphere of nitrogen, sodium hydride (1.2 g, 0.03 mol 60% dispersion in oil) was carefully added. The reaction mixture was left stirring for 15 minutes. 1-Bromo-3-chloro-propane (8.0 g, 0.05 mol) was added and the mixture was left stirring overnight. Ammonium chloride (2.0 g, 0.04 mol) was added, and after continued stirring for 30 minutes, the solution was poured onto water (300 ml). The mixture was extracted with dichloromethane (2×200 ml). The combined organic extracts were dried ($MgSO_4$), filtered and the solvent evaporated in vacuo. 10-(3-Chloropropyl)-10H-phenoxazine was obtained in quantitative yield as an oil and used without further purification. $R_f$: 0.68 ($SiO_2$; n-heptane/ethyl acetate (1:1).

Potassium iodide (10.0 g, 0.06 mol) was dissolved in methyl ethyl ketone (100 ml) and heated at reflux temperature for 1 h. The above chloride (5.2 g, 0.02 mol) was dissolved in methyl ethyl ketone (10 ml) and added. The mixture was heated at reflux temperature for 3 h. After cooling to about 60° C., (R)-3-piperidinecarboxylic acid ethyl ester tartrate (5.3 g, 0.0018 mol) and potassium carbonate (4.0 g, 0.028 mol) were added. The mixture was heated at reflux temperature for 24 h, and left stirring at room temperature for 24 h. After filtration on filter aid (celite) the solvent was removed by evaporation in vacuo. The residue was purified by column chromatography on silica gel (250 g) using a mixture of heptane and ethyl acetate (1:1) as eluent. This afforded 5.2 g (67%) of (R)-1-(3-(10H-phenoxazin-10-yl)-propyl)-3-piperidinecarboxylic acid ethyl ester as an oil. $R_f$: 0.25 ($SiO_2$; n-heptane/ethyl acetate=1:1).

The above ester (2.34 g, 0.006 mol) was dissolved in ethanol (25 ml) and and a solution of NaOH (0.9 g) in water (3.5 ml) was added. The mixture was stirred at room temperature for 2 h. Concentrated HCl was added until pH<1 (3.5 ml). Dichloromethane (150 ml) was added, followed by water (70 ml) and the phases were separated. The organic phase was dried ($MgSO_4$) and the solvent evaporated in vacuo, affording 1.8 g (77%) of product. To further purify the product, it was washed with diethyl ether, ethyl acetate and subsequently acetone, affording 1.2 g (50%) of the title compound.

M.p. 217–220° C. Calculated for $C_{21}H_{24}N_2N_2O_3$, HCl: C, 64.86%; H, 6.48%; N, 7.20%; Found: C, 64.56%; H, 6.70%; N, 6.89%.

Example 10

(S)-1-(3-(10,11-Dihydro-5H-dibenzo[b,f]azepin-5-yl-1-propyl)-3-piperidinecarboxylic Acid Hydrochloride To a solution of 10,11-dihydro-5H-dibenzo[b,f]azepine (8.1 g, 0.040 mol) in dry dibutyl ether (60 ml) kept under an atmosphere of nitrogen, sodium hydride (1.6 g, 0.04 mol, 60% dispersion in oil) was carefully added. The reaction mixture was heated at reflux temperature for 4 h and then allowed to cool to 80° C. 3-Bromo-1-propyl tetrahydro-2-pyranyl ether (10.7 g, 0.048 mol) was added and the mixture was heated at reflux temperature for 16 h. After cooling to room temperature, water (20 ml) was added, and the phases were separated. The organic phase was evaporated until dryness. The residue was dissolved in a mixture of methanol (150 ml) and 4N HCl (50 ml). The mixture was heated at reflux temperature for 15 minutes and then stirred for 1 h at room temperature. Water (250 ml) was added and the mixture was extracted with ethyl acetate (2×200 ml). The combined organic extracts were dried ($Na_2SO_4$), filtered and the solvent evaporated in vacuo. This afforded a residue which was purified by column chromatography on silica gel (200 g) using a mixture of n-heptane and ethyl acetate (3:2) as eluent. This afforded 5.5 g (54%) of 3-(10,11-dihydro-5H-dibenzo[b,f]azepin-5-yl)-1-propanol as an oil, that solidified upon cooling in a refrigerator overnight. $R_f$: 0.30 ($SiO_2$; n-heptane/ethyl acetate=1:1).

The above alcohol (2.5 g, 0.0099 mol) was dissolved in dry THF (20 ml) and triethylamine (2.0 ml) was added under a nitrogen atmosphere. Methanesulfonyl chloride (0.77 ml, 0.0099 mol) was added dropwise and when addition was complete the reaction mixture was stirred for 45 minutes and then filtered. Triethylamine (3.4 ml) was added to the filtrate, followed by (S)-3-piperidinecarboxylic acid ethyl ester tartrate (4.55 g, 0.015 mol). The mixture was heated at reflux temperature for 48 h, and left at room temperature for 7 days. After filtration on filter aid (celite) the solvent was removed by evaporation in vacuo. The residue was purified further by column chromatography on silica gel (200 g) using a mixture of dichloromethane and methanol (9:1) as eluent, affording 0.4 g (9%) of (S)-1-(3-(10,11-dihydro-5H-dibenzo[b,f]azepin-5-yl)-1-propyl)-3-piperidinecarboxylic acid ethyl ester as an oil. $R_f$: 0.30 ($SiO_2$; dichloromethane/methanol=9:1).

The above ester (0.35 g, 0.89 mmol) was dissolved in ethanol (3 ml) and 12N NaOH (0.26 ml) was added. The mixture was stirred at room temperature for 1.5 h and 4N HCl was added until pH<1 (1 ml). Dichloromethane (50 ml) was added and the phases were separated. The organic phase was dried ($MgSO_4$) and the solvent evaporated in vacuo. The residue was re-evaporated twice with acetone, affording after drying 0.2 g (62%) of the title compound as a white amorphous product.

HPLC retention time=21.36 minutes. Calculated for $C_{23}H_{28}N_2O_2$, HCl, 3/4 $H_2O$: C, 66.65%; H, 7.42%; N, 6.76%; Found: C, 66.99%; H, 7.48%; N, 6.36%.

Example 11

1-(3-(10,11-Dihydro-5H-dibenzo[b,f]azepin-5-yl)-1-propyl)-3-pyrrolidinacetic Acid Hydrochloride 3-(10,11-Dihydro-5H-dibenzo[b,f]azepin-5-yl)-1-propanol (2.0 g, 0.0079 mol, prepared as described in example 10) was dissolved in dry THF (25 ml) under an atmosphere of nitrogen, and triethylamine (2.75 ml) was added. Methanesulfonyl chloride (0.61 ml, 0.0079 mol) was added dropwise and when addition was complete the reaction mixture was stirred for 45 minutes. The mixture was filtered and 3-pyrrolidinacetic acid methyl ester (2.4 g, 0.012 mol) was added to the filtrate. The mixture was heated at reflux temperature for 4 h and then stirred at room temperature for 48 h. Triethylamine (2.2 ml) was added and the mixture was heated at reflux temperature for 24 h. After cooling to room temperature the solvent was removed by evaporation in vacuo. The residue was purified by column chromatography on silica gel (125 g) using a mixture of dichloromethane and methanol (9:1) as eluent, affording 0.9 g (27%) of 1-(3-(10,11-dihydro-5H-dibenzo[b,f]azepin-5yl)-1-propyl)-3-pyrrolidinacetic acid methyl ester as an oil. $R_f$: 0.15 ($SiO_2$; dichloromethane/methanol/acetic acid= 20:2:1).

The above ester (0.85 g, 0.0022 mol) was dissolved in ethanol (6 ml) and 0.5N NaOH was added. By continued addition of 0.25N NaOH pH was kept at approximately 12 for 3 days. Dilute HCl (approx. 1N) was added until pH=7, and the solvent was evaporated in vacuo. The residue was purified by column chromatography on silica gel (50 g) using a mixture of dichloromethane, methanol and acetic acid (20:2:1) as eluent. The product fractions were stripped with dichloromethane, affording 0.04 g (3.8%) of 1-(3-(10,11-dihydro-5H-dibenzo[b,f]azepin-5-yl)-1-propyl)-3-pyrrolidinacetic acid as an amorphous product.

HPLC retention time=21.66 minutes. $^1$H-NMR (400 MHz, $CDCl_3$) $\delta_H$ 1.68 (1H, m), 2.01 (2H, m), 2.15 (2H, m), 2.38 (2H, m), 2.63 (1H, m), 2.81 (1H, m), 2.95 (2H, m), 3.13 (6H, m), 3.80 (2H, t), 6.92 (2H, t), 7.01 (2H, m), 7.06–7.18 (4H, m).

Example 12

(R)-1-(3-(11H-10-Oxa-5-aza-5H-dibenzo[a,d] cyclohepten-5-yl)-1-propyl)-3-piperidinecarboxylic Acid Hydrochloride In a 500 ml roundbottom flask equipped with magnetical stirring, thermometer and addition funnel 5,11-dihydro-10-oxa-5-azadibenzo[a,d]cycloheptene (4.0 g, 0.02 mol, prepared in a similar way as described in *J. Med. Chem.*, 7, (1964), 609) was dissolved in dry toluene (50 ml) and 3-bromopropionyl chloride (4.2 g, 0.024 mol) was slowly added. The reaction mixture was heated to 95° C. for 30 minutes and then allowed to cool to room temperature. Under stirring 0.2N NaOH (10 ml) was added. More toluene was added (50 ml) and the phases were separated. The organic phase was washed with 0.2N NaOH (3×20 ml) until pH>10, and then with water (3×20 ml) and brine (20 ml). After drying ($MgSO_4$), the organic phase was evaporated in vacuo affording an oil. The product was obtained in quantitative yield and used for further reactions without purification.

The above amide (3.5 g, 0.01 mol) was dissolved in dry THF (20 ml) under a nitrogen atmosphere and cooled to 5° C. Sodium borohydride (0.31 g, 0.008 mol) was added followed by slow dropwise addition of boron trifluoride etherate (2.0 ml, 0.016 mol). The reaction mixture was left stirring overnight. Further amounts of sodium borohydride (1.2 g. 0.032 mol) and boron trifluoride etherate (5 ml, 0.040 mol) were supplied, and stirring was continued overnight. Water was added to dissolve precipitated salt, followed by ethyl acetate (100 ml). The phases were separated, and the aqueous phase was extracted with ethyl acetate (2×100 ml). The combined organic extracts were washed with water (4×100 ml) and brine (100 ml). After drying ($MgSO_4$) the solvent was removed by evaporation in vacuo and the crude product was purified by column chromatography on silica gel (200 g) with dichloromethane as eluent. This afforded 0.8 g (13%) of the product, 3-bromo-1-(11H-10oxa-5-aza-5H-dibenzo[a,d]cyclohepten-5-yl)propane. $R_f$: 0.62 ($SiO_2$; dichloromethane).

Potassium iodide (3.0 g, 0.018 mol) was dissolved in methyl ethyl ketone (50 ml) and heated at reflux temperature for 30 minutes. The above bromide (0.8 g, 0.0025 mol) was dissolved in methyl ethyl ketone (20 ml), and added. The mixture was heated at reflux temperature for 90 minutes. After cooling to about 60° C., (R)-3-piperidinecarboxylic acid ethyl ester tartrate (0.8 g, 0.0027 mol) and potassium carbonate (0.62 g, 0.0053 mol) were added. The mixture was heated at reflux temperature for 24 h, and left stirring at room temperature for 48 h. After filtration on filter aid (celite) the solvent was removed by evaporation in vacuo. The residue was purified by column chromatography on silica gel (100 g) using a mixture of heptane and ethyl acetate (1:1) as eluent. This afforded 0.4 g (37%) of (R)-1-(3-(11H-10-oxa-5-aza-5H-dibenzo[a,d]cyclohepten-5-yl)-1-propyl)-3-piperidinecarboxylic acid ethyl ester as an oil. $R_f$: 0.17 (SiO$_2$; n-heptane/ethyl acetate=1:1).

The above ester (0.37 g, 0.00094 mol) was dissolved in ethanol (5 ml) and a solution of NaOH (0.13 g) in water (0.5 ml) was added. The mixture was stirred at room temperature for 2 h. Concentrated HCl was added until pH<1 (0.5 ml). Dichloromethane (50 ml) was added, followed by water (10 ml) and the phases were separated. The organic phase was dried (MgSO$_4$) and the solvent evaporated in vacuo. The residue was re-evaporated twice with acetone and once with ethyl acetate, affording, after drying, 0.3 g (77%) of the title compound as an amorphous compound.

HPLC retention time=22.57 minutes. Calculated for C$_{22}$H$_{26}$N$_2$O$_3$, HCl, 1/2 C$_4$H$_8$O$_2$: C, 64.49%; H, 6.99%; N, 6.27%; Found: C, 64.32%; H, 7.05%; N, 5.99%.

Example 13

1-(3-(10,11-Dihydro-5H-dibenzo[b,f]azepin-5-yl)-1-propyl)-1,2,5,6tetrahydro-3-pyridinecarboxylic Acid Hydrochloride 3-(10,11-Dihydro-5H-dibenzo[b,f]azepin-5-yl)-1-propanol (1.75 g, 0.0069 mol, prepared as described in Example 4) was dissolved in THF (20 ml) and kept under an atmosphere of nitrogen. Triethylamine (1.44 ml) was added, followed by dropwise addition of methanesulfonyl chloride (0.54 ml, 0.0069 mol). When addition was complete the reaction mixture was stirred for 45 minutes. The reaction mixture was filtered and 1,2,5,6-tetrahydro-3-pyridinecarboxylic acid ethyl ester hydrochloride (1.99 g, 0.01 mol) and triethylamine (2.4 ml) were added. The mixture was stirred at room temperature for 9 days. More THF was added, the reaction mixture was filtered and the solvent was removed by evaporation in vacuo. The residue was purified by column chromatography on silica gel (100 g) using a mixture of heptane and ethyl acetate (1:1) as eluent. This afforded 2.1 g (78%) of 1-(3-(10,11-dihydro-5H-dibenzo[b,f]azepin-5-yl)-1-propyl)-1,2,5,6-tetrahydro-3-pyridinecarboxylic acid ethyl ester as an oil. $R_f$: 0.25 (SiO$_2$; n-heptane/ethyl acetate=1.1).

The above ester (1.7 g, 0.0044 mol) was dissolved in ethanol (10 ml) and 4N NaOH (2.7 ml) was added. The mixture was stirred at room temperature for 3 h. 4N HCl (3.8 ml) was added followed by dichloromethane (100 ml) and the phases were separated. The organic phase was dried (MgSO$_4$) and the solvent evaporated In vacuo, affording 1.3 g (76%) of the title compound as a white amorphous product.

HPLC retention time=21.16 minutes. Calculated for C$_{23}$H$_{26}$N$_2$O$_2$, HCl, H$_2$O: C, 66.26%; H, 7.01%; N, 6.72%; Found: C, 66.57%; H, 7.21%; N, 6.33%.

Example 14

(R)-1-(3-(6,7-Dihydro-5H-dibenzo[b,g]azocin-12-yl)-1-propyl)-3-piperidinecarboxylic Acid Hydrochloride In a 100 ml roundbottom flask equipped with magnetical stirring, thermometer and addition funnel, 5,6,7,12-tetrahydrodibenzo[b,g]azocine (2.1 g, 0.01 mol, prepared in a similar way as described in *Chem. Pharm. Bull* 26, (1978), 942) was dissolved in dry toluene (60 ml) and ethyl malonyl chloride (2.0 g, 0.013 mol) was slowly added. The reaction mixture was heated at reflux temperature for 2 h and then allowed to cool to room temperature. Under stirring, 0.2N NaOH (5 ml) and water (60 ml) were added. More toluene was added (100 ml) and the phases were separated. The organic phase was washed with water (3×75 ml) and brine (75 ml). After drying (MgSO$_4$), the organic phase was evaporated in vacuo affording 3.1 g (95%) of 3-(6,7-dihydro-5H-dibenzo[b,g]azocin-1 2-yl)-3-oxopropionic acid ethyl ester as an oil.

LiAlH$_4$ (1.4 g, 0.037 mol) was placed in a dry, 250 ml, three-necked, roundbottom flask, equipped with thermometer, magnetical stirring and addition funnel. Under nitrogen, dry toluene (60 ml) was added followed by slow addition of THF (6 ml). A temperature at 15–25° C. was assured by the use of a water/ice-bath. After stirring for 30 minutes, the above amide (3.0 g, 0.0093 mol) was dissolved in dry toluene (18 ml) and slowly added to the LiAlH$_4$-slurry at 20–25° C. The reaction mixture was left stirring overnight at room temperature. Water (1.5 ml) was slowly added dropwise, followed by 4N NaOH (1.5 ml) and finally water (4.5 ml). The resulting precipitate was filtered off on filter aid (celite). The toluene solution was dried (MgSO$_4$) and evaporated in vacuo. The crude residue was purified by column chromatography on silica gel (75 g), using a mixture of heptane and ethyl acetate (1:1) as eluent. This afforded 0.4 g (48%) of 3-(6,7-dihydro-5H-dibenzo[b,g]azocin-12-yl)-1-propanol, as an oil. $R_f$: 0.37 (SiO$_2$; n-heptane/ethyl acetate= 1:1).

The above alcohol (1.2 g, 0.0045 mol) was dissolved in toluene (25 ml) and triethylamine (1.5 ml) was added. Methanesulfonyl chloride (0.75 ml, 0.009 mol) was added dropwise and the reaction mixture was stirred for 2 h. Water (100 ml) was added, followed by further amounts of toluene (100 ml) and the phases were separated. The organic phase was dried (MgSO$_4$) and the solvent evaporated in vacuo affording a residue which was dissolved in methyl ethyl ketone (75 ml). To this solution, (R)-3-piperidinecarboxylic acid ethyl ester tartrate (2.1 g, 0.007 mol) and potassium carbonate (1.5 g, 0.011 mol) were added and the mixture was heated at reflux temperature for 24 h, and left stirring at room temperature for 8 days. After filtration on filter aid (celite) the solvent was removed by evaporation in vacuo. The residue was purified by column chromatography on silica gel (75 g) using a mixture of heptane and ethyl acetate (1:1) as eluent. This afforded 1.1 g (61%) of (R)-1-(3-(6,7-dihydro-5H-dibenzo[b,g]azocin-12-yl)-1-propyl)-3-piperidinecarboxylic acid ethyl ester as an oil. $R_f$: 0.29 (SiO$_2$; n-heptane/ethyl acetate=1:1).

The above ester (500 mg, 0.0012 mol) was dissolved in ethanol (7 ml) and a solution of NaOH (0.2 g) in water (1.5 ml) was added. The mixture was stirred at room temperature for 2 h, and concentrated HCl was added until pH<1 (0.75 ml). Dichloromethane (100 ml) was added, followed by water (50 ml) and the phases were separated. The organic phase was dried (MgSO$_4$) and the solvent evaporated in vacuo. The residue was re-evaporated with acetone, ethyl acetate was added and the product was filtered and washed with diethyl ether. This afforded, after drying, 0.4 g (71%) of the title compound as an amorphous compound.

HPLC retention time=22.70 minutes. Calculated for $C_{24}H_{30}ON_2O_2$, HCl, 1/4 $C_4H_8O_2$: C, 68.72%; H, 7.56%; N, 6.41%; Found: C, 69.12%; H, 7.94%; N, 6.12%.

Example 15

(R)-1-(3-(10,11-Dihydro-5H-dibenzo[a,d] cyclohepten-5-yl)-1-propyl)-3-piperidinecarboxylic Acid Hydrochloride In a 50 ml roundbottom flask equipped with magnetical stirring, thermometer and addition funnel, sodium hydride (0.8 g, 0.02 mol, 60% dispersion in oil) was suspended in dry toluene under an atmosphere of nitrogen. A solution of 10,11-dihydro-5H-dibenzo[a,d]cycloheptene-5-carbonitrile (3.0 g, 0.014 mol, prepared in a similar way as described in J. Med. Chem., 6 (1963), 251) in dry toluene (15 ml) was added. The reaction mixture was heated to reflux temperature in 30 minutes and then heated at reflux temperature for 150 minutes. After cooling to about 50° C., a solution of 3-bromopropyl tetrahydropyranyl ether (4.5 g, 0.02 mol) in dry toluene (6 ml) was added dropwise. The reaction mixture was heated at reflux temperature for 5 h and then left stirring at room temperature overnight. After filtration of precipitated salts, the solution was washed with 1N HCl (100 ml), diluted with more toluene (100 ml) and finally washed with water. After drying (MgSO$_4$), the organic phase was evaporated in vacuo affording 7.2 g (99%) of 5-(3-(tetrahydropyran-2-yloxy)-1-propyl)-10,11-dihydro-5H-dibenzo[a,d]cycloheptene-5-carbonitrile.

Under nitrogen, sodium amide (3.5 g, 0.045 mol, 50% suspension in toluene) was added to a 100 ml three-necked roundbottom flask. The above nitrile (4.0 g, 0.011 mol) was dissolved in dry toluene (50 ml) and added. The reaction mixture was heated at reflux temperature for 16 h. After cooling to room temperature, water was added with caution (100 ml). More toluene was added and the organic phase was washed with dilute HCl. After drying (MgSO$_4$), the organic phase was evaporated in vacuo affording 3.0 g (81%) of crude 2-(3-(10,11-dihydro-5H-dibenzo[a,d]cyclohepten-5-yl)-1-propyloxy)tetrahydropyran as an oil.

The above tetrahydropyran (3.0 g, 0.009 mol) was dissolved in methanol (30 ml). and 4N HCl (10 ml) was added. The reaction mixture was heated at reflux temperature for 15 minutes and left stirring at room temperature for 1 h. Water (50 ml) was added and the aqueous phase was extracted with ethyl acetate (3×75 ml). The combined organic extracts were dried (MgSO$_4$), filtered and the solvent evaporated in vacuo. This afforded a residue which was purified by column chromatography on silica gel (100 g) using a mixture of n-heptane and ethyl acetate (2:1) as eluent. This afforded 0.6 g (24%) of 3-(10,11-dihydro-5H-dibenzo[a,d]cyclohepten-5-yl)-1-propanol as an oil. $R_f$: 0.37 (SiO$_2$; n-heptane/ethyl acetate=1:1).

The above alcohol (0.55 g, 0.002 mol) was dissolved in toluene (25 ml) and triethylamine (1 ml) was added. Methanesulfonyl chloride (0.5 ml, 0.006 mol) was added dropwise and the reaction mixture was stirred for 2 h. Water (75 ml) was added, followed by a further amount of toluene (100 ml) and the phases were separated. The organic phase was dried (MgSO$_4$) and the solvent evaporated in vacuo affording a residue which was dissolved in methyl ethyl ketone (50 ml). To this solution, (R)-3-piperidinecarboxylic acid ethyl ester tartrate (1.0 g, 0.0033 mol) and potassium carbonate (0.75 g, 0.0055 mol) were added and the mixture was heated at reflux for 24 h, and then left stirring at room temperature for 72 h. After filtration on filter aid (hyflo) the solvent was removed by evaporation in vacuo. The residue was purified by column chromatography on silica gel (50 g) using a mixture of heptane and ethyl acetate (1:1) as eluent. This afforded 0.25 g (29%) of (R)-1-(3-(10,11-dihydro-5H-dibenzo[a,d]cyclohepten-5-yl)-1-propyl)-3-piperidinecarboxylic acid ethyl ester as an oil. $R_f$: 0.21 (SiO$_2$; n-heptane/ethyl acetate=1:1).

The above ester (240 mg, 0.00061 mol) was dissolved in ethanol (4 ml) and a solution of NaOH (0.1 g) in water (1 ml) was added. The mixture was stirred at room temperature for 2 h and concentrated HCl was added until pH<1 (0.4 ml). Dichloromethane (100 ml) was added, followed by water (50 ml) and the phases were separated. The organic phase was dried (MgSO$_4$) and the solvent evaporated in vacuo. The residue was re-evaporated with acetone, ethyl acetate was added and the product was filtered and washed with diethyl ether. This afforded, after drying, 0.2 g (73%) of the title compound as an amorphous product.

MS(EI) 363.2 (M$^+$-HCl, 15%). Calculated for $C_{24}H_{29}NO_2$, HCl, 3/2 H$_2$O: C, 67.52%; H, 7.74%; N, 3.28%; Found: C, 67.70%; H, 7.77%; N, 3.44%

Example 16

(R)-1-(3-Methoxy-10,11-dihydro-5H-dibenzo[b,f] azepin-5-yl)-1-propyl)-3-piperidinecarboxylic Acid Hydrochloride In a 100 ml roundbottom flask equipped with magnetical stirring, thermometer, N$_2$-inlet and addition funnel, 3-methoxy-10,11-dihydro-5H-dibenzo[b,f]azepine (1.2 g, 0.0053 mol) was dissolved in dry toluene (30 ml). Under nitrogen, ethyl malonyl chloride (1.01 g, 0.0067 mol) was slowly added. The reaction mixture was heated at reflux temperature for 2 h and then allowed to cool to room temperature. Under stirring a solution of 0.2N NaOH (2.5 ml) in water (30 ml) was added. More toluene was added (100 ml) and the phases were separated. The organic phase was washed with water (3×50 ml), and brine (50 ml). After drying (MgSO$_4$), the organic phase was evaporated in vacuo affording an oily residue. The product was obtained in quantitative yield and used for further reactions without purification.

LiAlH$_4$ (800 mg, 0.021 mol) was placed in a dry, 250 ml, three-necked, roundbottom flask, equipped with thermometer, mecanical stirring and addition funnel. Under nitrogen, dry toluene (40 ml) was added followed by slow addition of THF (4 ml). A temperature at 15–25° C. was assured by the use of a water/ice-bath. After stirring for 30 minutes, the above amide (1.96 g, 0.0053 mol) was dissolved in dry toluene (10 ml) and slowly added to the LiAlH$_4$-slurry, keeping the temperature at 20–25° C. The reaction mixture was left stirring overnight at room temperature. Water (1 ml) was added dropwise, followed by 4N NaOH (1 ml) and finally water (3 ml). The resulting precipitate was filtered off on filter aid (celite). The toluene solution was dried (MgSO$_4$) and the solvent was removed by evaporation in vacuo. The crude residue was purified by column chromatography on silica gel (75 g), using a mixture of heptane and ethyl acetate (1:1) as eluent. This afforded 0.9 g (61%) of the product, 3-(3-methoxy-10,11-dihydro-5H-dibenzo[b,f]azepin-5-yl)-1-propanol, as an oil. $R_f$: 0.25 (SiO$_2$; n-heptane/ethyl acetate=1:1).

The above alcohol (900 mg, 0.0032 mol) was dissolved in toluene (25 ml) and triethylamine (1.1 ml) was added. Methanesulfonyl chloride (1.0 ml, 0.013 mol) was added dropwise and the reaction mixture was stirred for 2 h. Water (100 ml) was added, followed by a further amount of toluene (100 ml) and the phases were separated. The organic phase was dried ($MgSO_4$) and the solvent evaporated in vacuo affording a residue which was dissolved in methyl ethyl ketone (50 ml). To this solution, (R)-3-piperidinecarboxylic acid ethyl ester tartrate (1.44 g, 0.0048 mol) and potassium carbonate (1.1 g, 0.008 mol) were added and the mixture was heated at reflux for 24 h, and left stirring at room temperature for 72 h. After filtration on filter aid (hyflo) the solvent was removed by evaporation in vacuo. The residue was purified by column chromatography on silica gel (50 g) using a mixture of heptane and ethyl acetate (1:1) as eluent. This afforded 0.2 g (14%) of 1-(3-(3-methoxy-10,11-dihydro-5H-dibenzo[b,f]azepin-5-yl)-1-propyl)-3-piperidinecarboxylic acid ethyl ester as an oil. $R_f$: 0.15 ($SiO_2$; n-heptane/ethyl acetate=1:1)

The above ester (190 mg, 0.00045 mol) was dissolved in ethanol (4 ml) and a solution of NaOH (0.1 g) in water (1 ml) was added. The mixture was stirred at room temperature for 2 h. Concentrated HCl was added until pH<1 (0.4 ml). Dichloromethane (100 ml) was added, followed by water (50 ml) and the phases were separated. The organic phase was dried ($MgSO_4$) and the solvent evaporated in vacuo. The residue was re-evaporated with acetone, ethyl acetate was added and the product was filtered and washed with diethyl ether. This afforded, after drying, 0.13 g (67%) of the title compound as an amorphous product.

HPLC retention time=22.25 minutes. Calculated for $C_{24}H_{30}N_2O_3$, HCl, $2H_2O$: C, 61.74%; H, 7.50%; N, 6.00%; Found: C, 61.83%; H, 7.51%; N, 5.98%.

Example 17

(R)-1-(3-(10-Methyl-11-oxo-10,11-dihydro-5H-dibenzo[b,e][1,4]diazepin-5-yl)-1-propyl)-3-piperidinecarboxylic Acid Hydrochloride To a solution of 11-oxo-10,11-dihydro-5H-dibenzo[b,e][1,4]diazepine (10 g, 0.048 mol, Synthesis. (1985), 550) in dry dimethylformamide (100 ml) kept under an atmosphere of nitrogen, sodium hydride (2.1 g, 0.052 mol, 60% dispersion in oil) was added, and the reaction mixture was stirred for 1.5 h. Iodomethane (3.27 ml, 0.052 mol) was slowly added keeping the temperature below 30° C. and the mixture was stirred overnight. The reaction mixture was quenched with saturated ammonium chloride (20 ml) and poured onto ice water (300 ml). The solid was filtered off and washed with plenty of water and dried. This yielded 10.4 g of crude 10-methyl-1-oxo-10,11-dihydro-5H-dibenzo[b,e][1,4] diazepine which was recrystallised from methanol (200 ml), to give 6.7 g (63%) of 10methyl-11-oxo-10,11-dihydro-5H-dibenzo[b,e][1,4]diazepine. M.p. 210–211° C.

$^1$H-NMR (200 MHz, DMSO-$d_6$) $\delta_H$ 3.37 (s, 3H, N—$CH_3$), 6.90 (t, 1H) 6.97–7.14 (m, 4H), 7.24–7.36 (m, 2H), 7.66 (dd, 1H), 7.91 (bs, 1H, NH).

10-Methyl-11-oxo-10,11-dihydro-5H-dibenzo[b,e][1,4]diazepine (5 g, 0.022 mol) was dissolved in dry THF (50 ml) under an atmosphere of nitrogen. n-Butyl lithium (9.1 ml, 0.025 mol, 23% solution in hexane) was slowly added with cooling on an ice bath and stirred for 30 minutes. A solution of 2-(3-bromo-1-propyloxy)tetrahydro-2H-pyran (6.28 g, 0.027 mol) in dry THF (10 ml) was slowly added at room temperature. The reaction mixture was heated to 60° C. for 1 h and stirred at room temperature overnight. The reaction mixture was quenched with saturated ammonium chloride (20 ml) and poured onto ice water (200 ml). The mixture was extracted with dichloromethane (3×150 ml). The combined organic extracts were washed with water (2×80 ml), dried ($MgSO_4$), filtered and the solvent evaporated in vacuo. This afforded a residue (9.8 g) which was purified by column chromatography on silica gel (900 ml) using a mixture of dichloromethane and ethyl acetate (6:1) as eluent. This yielded 5.7 g (69%) 10-methyl-5-(3-(tetrahydro-2H-pyran-2-yloxy)-1-propyl)-5,10-dihydro-5H-dibenzo[b,e][1,4]-diazepin-11-one as an oil. $R_f$: 0.57 ($SiO_2$; Dichloromethane/ethyl acetate=8:2).

10-Methyl-5-(3-(tetrahydro-2H-pyran-2-yloxy)-1-propyl)-5,10-dihydro-5H-dibenzo[b,e][1,4]diazepin-11-one (5.6 g, 0.015 mol) was dissolved in a mixture of glacial acetic acid (40 ml), THF (20 ml) and water (10 ml), and the mixture was heated at 45° C. for 6 h. Water (200 ml) was added and the mixture extracted with ethyl acetate (4×100 ml). The combined organic extracts were washed with water (4×100 ml), dried ($MgSO_4$), filtered and the solvent evaporated in vacuo. This afforded a residue (5.3 g) which was purified by column chromatography on silica gel (500 ml) using a mixture of ethyl acetate and n-heptane (3:1) as eluent. This afforded 2.3 g (53%) of 10-methyl-5-(3-hydroxy-1-propyl)-5,10-dihydro-5H-dibenzo[b,e][1,4] diazepin-11-one as white crystals. $R_f$: 0.34 ($SiO_2$; ethyl acetate/n-heptane=3:1). M.p. 177–178° C.

10-Methyl-5-(3-hydroxy-1-propyl)-5,10-dihydro-5H-dibenzo[b,e][1,4]diazepin-11-one (2 g, 0.007 mol) was dissolved in a mixture of dry THF (50 ml) and triethylamine (3 ml) under an atmosphere of nitrogen. Methanesulfonyl chloride (0.69 ml, 0.009 mol) in THF (10 ml) was added dropwise and the reaction mixture was stirred for 1 h. The solvent was removed by evaporation in vacuo and the residue was dissolved in dichloromethane (200 ml). The organic solution was washed with water (3×50 ml), dried ($MgSO_4$), filtered and the solvent evaporated in vacuo. This afforded 3.0 g 3-(11-oxo-10-methyl-10,11-dihydro-5H-dibenzo[b,e][1,4]diazepin-5-yl)-1-propylmethanesulfonate as a syrup.

A mixture of the above methanesulfonate (2.5 g, 0.007 mmol), (R)-3-piperidinecarboxylic acid ethyl ester tartrate (2.56 g, 0.0083 mol) and dry potassium carbonate (5.81 g, 0.042 mol) in methyl ethyl ketone (50 ml) was heated at reflux temperature for 60 h under an atmosphere of nitrogen. The reaction mixture was filtered and the filter cake washed with plenty of ethyl acetate. The combined organic phases were washed with saturated ammonium chloride (1×100 ml), water (2×100 ml), brine (1×50 ml), dried ($MgSO_4$), filtered and the solvent evaporated in vacuo. The crude product 3.13 g of (R)-1-(3-(10-methyl-11-oxo-10,11-dihydro-5H-dibenzo[b,e][1,4]-diazepin-5-yl)-1-propyl)-3-piperidinecarboxylic acid ethyl ester was used without further purification.

The above ester (2.5 g, 0.006 mol) was dissolved in a mixture of ethanol (20 ml) and water (10 ml). Sodium hydroxide (0.3 g, 0.007 mol) was added and the reaction mixture stirred overnight at room temperature. Water (300 ml) was added and the mixture was washed with diethyl ether (2×100 ml) and ethyl acetate (1×100 ml). The aqueous phase was acidified with concentrated HCl (2.2 ml) and washed with dichloromethane (3×100 ml). Evaporation of the water gave a foam which was trituated with a mixture of acetone and 2-propanol (1:1) (3×50 ml) and evaporated in vacuo. The residue was dissolved in a mixture of acetone (100 ml) and 2-propanol (30 ml). Diethyl ether (100 ml) was added and the mixture was stirred overnight. The precipitate was filtered off and washed with diethyl ether and dried in vacuo to give 1.14 g (45%) of the title compound as white crystals.

M.p. 204–206° C. Calculated for $C_{23}H_{27}N_3O_3$, HCl, 7/4 $H_2O$: C, 59.86%; H, 6.88%; N, 9.11%; Found C, 59.93%; H, 6.97%; N. 8.97%.

Example 18

(R)-1-(3-(9(H)-Oxo-10H-acridin-10-yl)-1-propyl)-3-piperidinecarboxylic Acid Hydrochloride To a solution of acridone (15 g, 0.077 mol) in dry dimethylformamide (200 ml), sodium hydride (3.7 g, 0.092 mol. 60% dispersion in mineral oil) was added in 4 portions under an atmosphere of nitrogen. The reaction mixture was stirred until gas evolution had ceased. A solution of 2-(3-bromo-1-propyloxy)tetrahydro-2H-pyran (21.7 g, 0.092 mol) in dry dimethylformamide (100 ml) was added dropwise. The reaction mixture was heated to 80° C. for 4 h and stirred overnight at room temperature. The reaction mixture was poured onto ice water (800 ml) and extracted with ethyl acetate (4×200 ml). The combined ethyl acetate extracts were washed with water (3×300 ml), dried ($MgSO_4$), filtered and the solvent evaporated in vacuo. The residue was dissolved in diethyl ether (150 ml) and unchanged starting material was filtered off. The solvent was evaporated in vacuo and the residue was crystallised from 96% ethanol (150 ml), filtered and washed with ethanol (96%, 30 ml) and diethyl ether (50 ml). This procedure was repeated twice, yielding 8.5 g (33%) of 10-(3-(tetrahydro-2H-pyran-2-yloxy)-1-propyl)acridin-9-one as yellowish crystals. M.p. 140.5–141.5° C.

$^1$H-NMR (200 MHz, CDCl$_3$) $\delta_H$ 1.50–2.00 (m, 6H), 2.22 (m, 2H), 3.61 (m, 2H), 3.97 (m, 2H), 4.53 (dt, 2H), 4.63 (t, 1H), 7.24–7.32 (dd, 2H), 7.61–7.76 (m, 4H), 8.58 (dd, 2H).

10-(3-(Tetrahydro-2H-pyran-2-yloxy)-1-propyl)acridin-9-one was transformed into the title compound using the same procedure as described in Example 17.

M.p. >280° C. $^1$H-NMR (400 MHz, DMSO-d$_6$) $\delta_H$ 1.48 (bs, 1H), 1.89 (bm, 2H), 2.02 (bd, 1H), 2.30 (bs, 2H), 2.98 (bd, 2H), 3.42 (bm, 4H), 3.62 (bs, 1H), 4.57 (t, 2H, N—CH$_2$—CH$_2$—), 7.37 (t, 2H), 7.86 (dt, 2H), 7.97 (d, 2H), 8.38 (dd, 2H), 11.00 (bs, 1H), 12.85 (bs, 1H).

What is claimed is:

1. A compound of formula I

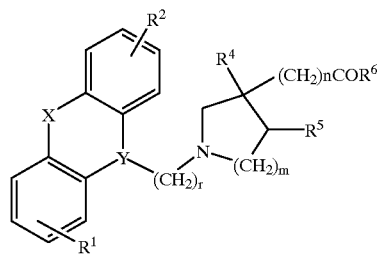

(I)

wherein

R$^1$ and R$^2$ independently are hydrogen, halogen, trifluoromethyl, C$_{1-6}$-alkyl or C$_{1-6}$-alkoxy;

Y is a nitrogen atom;

X is —S—;

r is 2, 3 or 4;

m is 2;

n is 0;

R$^4$ and R$^5$ are hydrogen or form a bond; and

R$^6$ is OH;

as a pharmaceutically acceptable acid addition salt.

2. The compound according to claim 1 which is (R)-1-(3-(10H-Phenothiazin-10-yl)-1-propyl)-3-piperidinecarboxylic acid, as the pharmaceutically acceptable acid addition salt.

3. The compound according to claim 1 which is (R)-1-(3-(2-Trifluoromethyl-10H-phenothiazin-10-yl)-1-propyl)-3-piperidinecarboxylic acid, as the pharmaceutically acceptable acid addition salt.

4. A pharmaceutical composition comprising a compound according to claim 1 together with a pharmaceutically acceptable carrier or diluent.

5. The pharmaceutical composition according to claim 4, wherein the compound is present in an amount between 0.5 mg and 1000 mg per unit dose.

* * * * *